(12) United States Patent
Farr et al.

(10) Patent No.: US 7,357,796 B2
(45) Date of Patent: Apr. 15, 2008

(54) PHOTOTHERAPEUTIC WAVE GUIDE APPARATUS

(75) Inventors: Norman E. Farr, Monument Beach, MA (US); William E. Wieler, Pocasset, MA (US)

(73) Assignee: CardioFocus Corporation, Norton, MA (US)

( * ) Notice: Subject to any disclaimer, the term of this patent is extended or adjusted under 35 U.S.C. 154(b) by 121 days.

(21) Appl. No.: 11/059,423

(22) Filed: Feb. 16, 2005

(65) Prior Publication Data
US 2005/0171520 A1    Aug. 4, 2005

Related U.S. Application Data

(60) Division of application No. 10/200,357, filed on Jul. 22, 2002, now Pat. No. 6,953,457, which is a continuation of application No. 09/357,355, filed on Jul. 14, 1999, now Pat. No. 6,423,055.

(51) Int. Cl.
    *A61B 18/18*    (2006.01)
(52) U.S. Cl. .............................. 606/15; 606/7; 607/89
(58) Field of Classification Search ................ 606/7–9, 606/13–18; 607/88, 89, 92–94; 128/898
See application file for complete search history.

(56) References Cited

U.S. PATENT DOCUMENTS

| | | | |
|---|---|---|---|
| 3,821,510 A | 6/1974 | Muncheryan | |
| 4,224,929 A | 9/1980 | Furihata | |
| 4,273,109 A | 6/1981 | Enderby | |
| 4,625,724 A | 12/1986 | Suzuki et al. | |
| 4,701,166 A | 10/1987 | Groshong et al. | |
| 4,718,417 A | 1/1988 | Kittrell et al. | |
| 4,770,653 A * | 9/1988 | Shturman | 606/7 |
| 4,781,681 A * | 11/1988 | Sharrow et al. | 604/103.07 |
| 4,819,632 A * | 4/1989 | Davies | 606/15 |
| 4,852,567 A | 8/1989 | Sinofsky | |
| 4,878,725 A | 11/1989 | Hessel et al. | |
| 4,961,738 A | 10/1990 | Mackin | |
| 5,071,417 A | 12/1991 | Sinofsky | |
| 5,078,681 A | 1/1992 | Kawashima | |
| 5,125,925 A | 6/1992 | Lundahl | |
| 5,140,987 A | 8/1992 | Schuger et al. | |
| 5,188,632 A | 2/1993 | Goldenberg | |
| 5,188,634 A * | 2/1993 | Hussein et al. | 606/7 |
| 5,190,538 A | 3/1993 | Hussein et al. | |
| 5,242,438 A | 9/1993 | Saadatmanesh | |
| 5,261,904 A | 11/1993 | Baker et al. | |
| 5,330,465 A | 7/1994 | Doiron et al. | |

(Continued)

FOREIGN PATENT DOCUMENTS

EP    0299448    7/1988

(Continued)

*Primary Examiner*—A. Farah
(74) *Attorney, Agent, or Firm*—Thomas J. Engellenner; Michael P. Doyle; Nutter McClennen & Fish, LLP

(57) ABSTRACT

Methods and apparatus are disclosed for forming annular lesions in tissue. The methods include introduction of an optical apparatus proximate to a tissue site, via, for example, a catheter. The optical apparatus includes a pattern-forming optical wave guide in communication with a light transmitting optical fiber. Energy is transmitted through the optical fiber, such that radiation is propagated through the optical fiber and the wave guide projects an annular light pattern, e.g., a circle or a halo.

19 Claims, 9 Drawing Sheets

U.S. PATENT DOCUMENTS

| | | | |
|---|---|---|---|
| 5,350,375 A | 9/1994 | Deckelbaum et al. | |
| 5,368,564 A | 11/1994 | Savage | |
| 5,380,317 A * | 1/1995 | Everett et al. | 606/15 |
| 5,395,362 A | 3/1995 | Sacharoff | |
| 5,427,119 A | 6/1995 | Swartz et al. | |
| 5,445,608 A * | 8/1995 | Chen et al. | 604/20 |
| 5,464,404 A | 11/1995 | Abela et al. | |
| 5,497,774 A | 3/1996 | Swartz et al. | |
| 5,507,725 A | 4/1996 | Savage et al. | |
| 5,575,766 A | 11/1996 | Swartz et al. | |
| 5,613,965 A | 3/1997 | Muller | |
| 5,693,043 A * | 12/1997 | Kittrell et al. | 606/15 |
| 5,759,619 A | 6/1998 | Jin | |
| 5,800,482 A | 9/1998 | Pomeranz et al. | |
| 5,830,209 A | 11/1998 | Savage et al. | |
| 5,833,682 A * | 11/1998 | Amplatz et al. | 606/15 |
| 5,885,278 A | 3/1999 | Fleischman | |
| 5,904,651 A | 5/1999 | Swanson et al. | |
| 5,908,415 A | 6/1999 | Sinofsky | |
| 5,938,660 A | 8/1999 | Swartz et al. | |
| 5,947,959 A | 9/1999 | Sinofsky | |
| 5,995,875 A | 11/1999 | Blewett et al. | |
| 6,012,457 A * | 1/2000 | Lesh | 128/898 |
| 6,024,740 A | 2/2000 | Lesh et al. | |
| 6,071,279 A | 6/2000 | Whayne et al. | |
| 6,071,282 A | 6/2000 | Fleischman | |
| 6,120,496 A | 9/2000 | Whayne et al. | |
| 6,146,379 A | 11/2000 | Fleischman et al. | |
| 6,164,283 A | 12/2000 | Lesh | |
| 6,214,002 B1 | 4/2001 | Fleischman et al. | |
| 6,235,025 B1 | 5/2001 | Swartz et al. | |
| 6,245,064 B1 | 6/2001 | Lesh et al. | |
| 6,251,104 B1 * | 6/2001 | Kesten et al. | 606/15 |
| 6,251,109 B1 | 6/2001 | Hassett et al. | |
| 6,270,492 B1 | 8/2001 | Sinofsky | |
| 6,394,949 B1 | 5/2002 | Crowley et al. | |
| 6,416,511 B1 | 7/2002 | Lesh et al. | |
| 6,423,055 B1 | 7/2002 | Farr et al. | |
| 6,423,058 B1 | 7/2002 | Edwards et al. | |
| 6,502,576 B1 | 1/2003 | Lesh | |
| 6,503,247 B2 | 1/2003 | Swartz et al. | |
| 6,514,249 B1 | 2/2003 | Maguire et al. | |
| 6,544,262 B2 | 4/2003 | Fleischman | |
| 6,558,375 B1 | 5/2003 | Sinofsky et al. | |
| 6,572,609 B1 * | 6/2003 | Farr et al. | 606/15 |
| 6,579,285 B2 | 6/2003 | Sinofsky | |
| 6,605,055 B1 | 8/2003 | Sinofsky | |
| 6,605,084 B2 | 8/2003 | Acker et al. | |
| 6,626,900 B1 * | 9/2003 | Sinofsky et al. | 606/15 |
| 6,635,054 B2 | 10/2003 | Fjield et al. | |
| 6,669,655 B1 | 12/2003 | Acker et al. | |
| 6,676,656 B2 | 1/2004 | Sinofsky | |
| 6,953,457 B2 * | 10/2005 | Farr et al. | 606/15 |
| 6,997,924 B2 * | 2/2006 | Schwartz et al. | 606/15 |
| 2002/0091383 A1 | 7/2002 | Hooven | |
| 2002/0115995 A1 | 8/2002 | Lesh et al. | |
| 2002/0120264 A1 | 8/2002 | Crowley et al. | |
| 2002/0183729 A1 | 12/2002 | Farr et al. | |
| 2002/0183739 A1 | 12/2002 | Long | |
| 2003/0050632 A1 | 3/2003 | Fjield et al. | |
| 2003/0065307 A1 | 4/2003 | Lesh | |
| 2003/0111085 A1 | 6/2003 | Lesh | |
| 2003/0120270 A1 | 6/2003 | Acker | |
| 2003/0171746 A1 | 9/2003 | Fleischman | |
| 2004/0054360 A1 | 3/2004 | Schwartz et al. | |

FOREIGN PATENT DOCUMENTS

| | | |
|---|---|---|
| EP | 0311458 | 10/1988 |
| WO | WO 9737714 | 10/1997 |
| WO | WO 0067832 | 11/2000 |

* cited by examiner

PHOTOTHERAPEUTIC WAVE GUIDE APPARATUS

CROSS-REFERENCE TO RELATED APPLICATIONS

This application is a divisional of U.S. patent application Ser. No. 10/200,357, filed Jul. 22, 2002, now U.S. Pat. No. 6,953,457 entitled "Phototherapeutic Wave Guide Apparatus," which is a continuation of U.S. patent application Ser. No. 09/357,355, filed Jul. 14, 1999, entitled "Phototherapeutic Wave Guide Apparatus," now U.S. Pat. No. 6,423,055.

FIELD OF THE INVENTION

The technical field of this invention is phototherapy and, in particular, methods and devices which employ optical fibers and flexible light waveguides to deliver radiation to a targeted site.

BACKGROUND OF THE INVENTION

Destruction of cellular tissues in situ has been used in the treatment of diseases and medical conditions alone or as an adjunct to surgical removal procedures. These methods are often less traumatic than surgical procedures and may be the only alternative where surgical procedures are unfeasible. Phototherapeutic treatment devices, e.g., lasers, have the advantage of using intense light energy which is rapidly attenuated to a non-destructive level outside of the target region. However, blood and/or other body fluids greatly diminish the effectiveness of several of these light energy sources as the radiation passes from an energy source, e.g., a laser source, through the body fluid to a treatment site. For example, the energy can be scattered or be absorbed by blood and other body fluids between the energy source and the tissue treatment site.

A common medical application of lasers is in the irradiation of tissue, both internal and external. For external treatment, the laser energy can be applied directly. However, where a procedure requires irradiation of internal tissues that are not readily accessible to external energy sources, the use of catheter-type devices to deliver coherent radiation to the treatment site is common. Typical applications requiring use of laser catheters are found in the treatment of various anatomical structures and conditions within the cardiovascular system.

Microwave, radio frequency, and acoustical (ultrasound) devices as well tissue destructive substances have also been used to destroy malignant, benign and other types of aberrant cells in tissues from a wide variety of anatomical sites and organs. Tissues sought to be treated include isolated carcinoma masses and, more specifically, organs such as the prostate, bronchial passage ways, passage ways to the bladder, passage ways to the urethra, and various passage ways into the thoracic area, e.g., the heart.

Devices useful for the treatment of such disease states or conditions typically include a catheter or a cannula which can be used to carry an energy source or waveguide through a lumen to the zone of treatment. The energy is then emitted from the catheter into the surrounding tissue thereby destroying the diseased tissue, and sometimes surrounding tissue.

Catheters have been utilized in the medical industry for many years. One of the greatest challenges in using a catheter is controlling the position and placement of the distal portion of the catheter from a remote location outside of the subject's body. Some catheters have features designed to aid in steering the catheter and overcoming this challenge. However, several significant problems are still encountered with catheters.

Careful and precise control over the catheter is required during critical procedures which ablate tissue within the heart. Such procedures are termed "electrophysiological" therapy and are becoming widespread for treatment of cardiac rhythm disturbances. During these procedures, an operator guides a catheter through a main artery or vein into the interior of the heart which is to be treated. The operator manipulates a mechanism to cause an electrode which is carried on the distal tip of the catheter into direct contact with the tissue area to be treated. Energy is applied from the electrode into the tissue and through an indifferent electrode (in a uni-polar electrode system) or to an adjacent electrode (in a bi-polar electrode system) to ablate the tissue and form a lesion. The irradiation of tissue must be accomplished with great precision as the danger of also damaging other adjacent tissue is always present, especially when the process occurs remotely at the distal end of a relatively long catheter.

One partial solution to this problem has been to "map" the area to be treated prior to a procedure. Cardiac mapping can be used prior to ablation to locate aberrant conductive pathways within the heart. The aberrant conductive pathways are called arrhythmias. Mapping of the heart identifies regions along these pathways, termed "foci", which are then ablated to treat the arrhythmias.

During laser ablation procedures, a catheter serves to deliver a fiber optic wave guide to the target region. Radiation transmitted through the optical fiber essentially vaporizes the targeted tissue to achieve the desired therapeutic goals of the procedure. Complete destruction of target tissue, with the exception of certain narrow and specific cardiac treatments, is generally limited to cardiological applications, e.g., removal of a blockage. In electrophysiological treatments, total destruction of target tissue (ablation) is not necessary, but controlled denaturation of tissue to affect its electrophysiological properties is required.

Within the heart, variations in cardiac tissue characteristics, perhaps as the result of scarring from previous cardiac trauma, can present vastly different tissue that react differently to the laser energy source. For example, absorption characteristics of normal tissue can be much different from tissue that is heavily scarred. In addition, the trabecular nature of the endocardium increases the difficulty because the laser radiation must reach a highly contoured or folded target tissue surface. As a result, temperatures of the tissue surface where the laser energy is incident can be much higher for some tissue than for others. In the treatment of cardiac tissue, the dynamic state of the heart tissue further complicates the situation in that the heart is constantly moving during treatment. Thus, incorporation of fixation means to maintain the position of the distal end of the laser catheter with respect to the target tissue site is often required.

There are drawbacks with many of the currently available catheters and treatments. Oftentimes it is difficult, if not impossible, to maneuver the instrument into small passage ways, such as a ventricle, without damaging the surrounding tissue. Most therapeutic treatments require that the apparatus is in contact with the tissue and with blood and/or other body fluids. Additionally, focusing the ablative energy onto the tissue site to be treated can be problematic, especially when vital organs surround the diseased tissue. Therefore, it would be desirable to focus ablative energy onto a specific treatment area wherein surrounding tissue is not degraded, the energy source is not in direct contact with the tissue and blood and body fluids are not coagulated or destroyed.

SUMMARY OF THE INVENTION

The present invention circumvents the problems described above by delivering energy, e.g., laser light or other ablative energy, in an annular pattern without requiring direct contact with an energy source, e.g. a laser (via fiber), with the targeted tissue. This indirect contact with the targeted tissue provides an advantage that damage to surrounding tissues is minimized or eliminated. More specifically, in cardiac therapy, another advantage is that an annular conduction block is created about the pulmonary vein orifice, thereby eliminating aberrant wave conduction.

In one embodiment, the present invention includes an apparatus for inducing phototherapeutic processes in tissue which can include ablation and/or coagulation of the tissue. Typically the optical apparatus is contained within a catheter including a flexible elongate member having a proximal end, a distal end and a longitudinal first lumen extending therebetween. The distal end of the flexible elongate member is open or includes a transparent cap, a centering balloon, or a centering coil. The optical apparatus of the invention can be slidably extended within the first lumen for projecting light through or from the distal end of the flexible member. Alternatively, the optical fiber and other light projecting elements can be fixed in place with the catheter.

The optical apparatus of the invention includes an optical wave guide for projecting an annular pattern of light and a light transmitting optical fiber. Radiation, e.g., infrared, visible or ultraviolet light is propagated through the optical fiber which is in communication with the pattern-forming wave guide. The wave guide/lens is configured to project an annular light pattern such that an annular lesion is formed in tissue. In one embodiment, the annular light pattern expands over distance and is in the form of a ring or a halo. The optical apparatus includes a graded intensity lens (GRIN) or standard refractive optics in addition to the optical wave guide to project the annular light pattern.

In certain embodiments, the optical apparatus of the invention is slidably positioned within the lumen of a catheter proximate to a tissue site. The catheter can include a balloon member fixedly attached to the catheter. Injection of a solution or gas expands the balloon, thereby forcing blood and/or other body fluids from the tissue site. Positioning the optical apparatus permits control over the size of the forwardly projected annular ring to be dynamically changed to accommodate varied pulmonary vein diameters.

The present invention also pertains to methods for forming an annular lesion in a tissue by phototherapeutic processes in tissue which can include ablation and/or coagulation of the tissue. The methods include introduction of an optical apparatus proximate to a tissue site via, for example, a catheter. The optical apparatus includes a pattern-forming optical wave guide that is in communication with a light transmitting optical fiber. Energy is transmitted through the optical fiber, such that radiation propagated through the optical fiber and wave guide projects an annular light pattern, e.g., a circle or a halo. By these methods, an annular lesion can be formed in a targeted tissue. In certain embodiments, the tissue forms a lumen, e.g., vascular, atrial, ventricular, aterial, brachial, or uretral lumen. Preferably the methods include projecting an annular light pattern through a graded intensity lens that is adjacent to the optical wave guide. This additional step forwardly projects the light pattern.

The present invention further pertains to methods for forming annular lesions in cardiac tissue, e.g., trabecular tissue, by phototherapeutic processes which can include ablation and/or coagulation of the tissue. The methods include introduction of an optical apparatus proximate to the cardiac tissue via, for example, a catheter. The optical apparatus includes a pattern-forming optical wave guide in communication with a light transmitting optical fiber. Energy is transmitted through the optical fiber, such that radiation is propagated through the optical fiber, the wave guide and GRIN lens to forwardly project an annular light pattern, e.g., a circle or a halo. In a preferred embodiment, a balloon is inflated against the tissue, thereby forcing blood and/or body fluids away from the tissue targeted for treatment. Light energy is then passed through the optical apparatus onto the targeted tissue such that an annular image is projected onto the site which causes ablation, coagulation or photochemical processes to occur.

The present invention also pertains to methods for treating or preventing atrial arrhythmias by phototherapeutic processes in atrial tissue. These processes can include ablation and/or coagulation of the tissue. The methods include introducing an optical apparatus proximate to atrial tissue via, for example, a catheter. The optical apparatus includes an optical wave guide in communication with a light transmitting optical fiber. Energy is transmitted through the optical fiber, such that radiation is propagated through the optical fiber and the wave guide projects an annular light pattern. The annular light pattern forms an annular lesion in the atrial tissue, thereby treating or preventing atrial arrhythmias.

The methods of the invention can be performed therapeutically or prophylactically. In one embodiment, the treatment method is performed on the atrial wall around the atrial/ pulmonary vein juncture or around the pulmonary vein, or within the pulmonary vein. A circular or ring-like section within the pulmonary vein is created by the method of the invention. Formation of one or more circular lesions about the outside or inside diameter of the vein, impedes the conduction of irregular electrical waves to the atrium.

BRIEF DESCRIPTION OF THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE INVENTION

Figure 1:
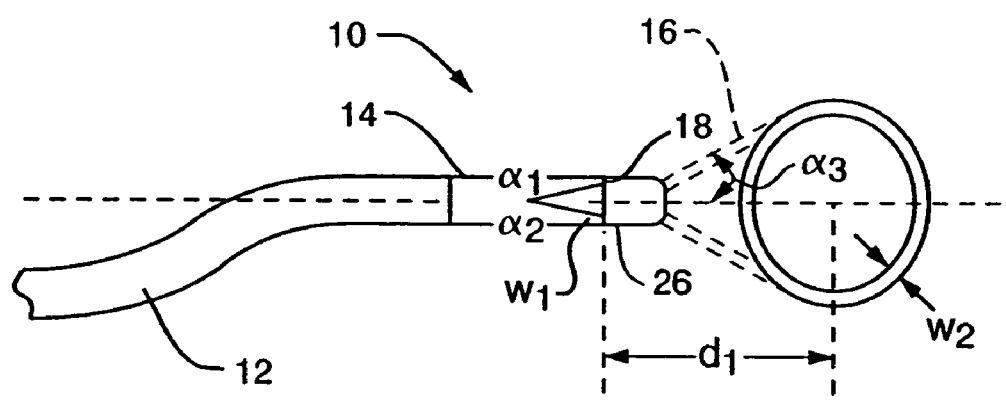
FIG. 1 is a schematic view of an optical apparatus of the invention which projects an annular beam of light from a modified wave guide.

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

The present invention is based, at least in part, on a discovery that the present invention can be used for inducing hyperthermia, coagulation or phototherapeutic processes in tissue, e.g., ablation, degradation, or destruction of tissue, at a specified site in tissue without harming the surrounding tissue. The results are surprising and unexpected since the efficiency and efficacy of coherent light is generally diminished by light scatter, formation of "hot spots" due to inefficient light scatter, by the limitation that the light emitted from an optical fiber continues in a straight path, and/or from interaction(s) with blood and/or body fluids which surround a tissue site to be treated.

Prior to this invention, the energy emitter, e.g., a laser source, ultraviolet light, microwave radiation, radio-frequency, etc., has generally been required to be in contact with the tissue to effect a therapeutic or prophylactic treatment. In contrast to known apparatuses and methods, the present invention does not require direct contact between the energy source, e.g., a laser source, and the tissue site to be treated. Moreover, in certain embodiments the methods and apparatus of the invention circumvent the drawbacks of having blood or body fluid coagulate, degrade or be destroyed in the treatment area proximate to the targeted tissue due to interactions with the applied energy.

In one embodiment, the present invention is drawn to an apparatus for inducing phototherapeutic processes in tissue. These processes can include ablation and/or coagulation. Typically the optical apparatus is contained within a catheter including a flexible elongate member having a proximal end, a distal end and a longitudinal first lumen extending therebetween. The distal end or a portion of the distal end of the flexible elongate member is open, transparent, or includes a transparent cap. The optical apparatus of the invention can be slidably extended within the first lumen for projecting light through or from a distal end portion of the flexible member.

The optical apparatus of the invention includes a pattern-forming optical wave guide for annularly projecting a pattern of light and a light transmitting optical fiber. Radiation is propagated through the optical fiber which is in communication with the wave guide. The wave guide is configured to forwardly project an annular light pattern such that an annular lesion is formed in tissue. Typically, the annular light pattern is projected at an angle between about 20 and 45 degrees from the center plane of the optical fiber. In one embodiment, the annular light pattern expands over distance and is in the form of a ring or a halo. Preferably, the optical apparatus further includes a graded intensity lens (GRIN) adjacent to the optical wave guide for attenuating any aberrations in the light pattern.

The present invention provides the advantage that the annular light pattern is forwardly projected. The invention further provides that the angle of projection can be attenuated by a GRIN lens and/or by the dimensions of a balloon, described infra, located proximate to the optical apparatus. In contrast, current apparatus' project light perpendicular to the central axis of the energy conduit, e.g., the optical fiber/wave guide. These apparatus, therefore, do not provide the ability to focus an annular ring about a preselected site in front of the light emitting apparatus as provided by the present invention. Consequently, the present invention provides the ability to focus energy onto a specific site, unlike cryogenic or sonic techniques which treat a site along with tissue which surrounds the site due to energy dissipation about the treatment site.

The term "phototherapeutic" is intended to include photoablative, photochemical and photothermal processes which are therapeutic and/or prophylactic in a subject.

The terms "ablate" or "ablation" or "photothermal" are well recognized in the art and are intended to include thermal coagulation and/or removal of tissues which are necrotic, damaged, or are aberrant in nature. Ablation also includes the desiccation of tissue by the application of heat. For example, an ablating energy, such as those described above, would be one that would cause the tissue to reach a temperature of between about 60-90° C. Ablation increases the physiological temperature of a tissue by energetic stimulation to a temperature which degrades or eradicates tissue, thereby removing diseased tissue from a localized area Ablation can be used as a therapeutic treatment, where diseased or otherwise unwanted tissue or cells exist, or as a preventative treatment to inhibit exigent physiological aberrations, e.g., arrhythmias e.g., fibrillations or flutters, growth of undesirable tissue or cells in a specific region of an organ or viscera. In order to obtain destruction of tissue exclusively by thermal effects, it is necessary for the energy to be able to reach a threshold of destruction referred to as the "thermal dose". This threshold is a function of temperature reached and of the duration of the application. Therefore, ablation, to some degree, is based on the rise of the local temperature of tissue.

The term "coagulation" is well recognized in the art and is intended to mean the action whereby cells and/or body fluids within a treated tissue site are caused to become necrosed, thickened and/or lose the ability to conduct electrical activity, thereby resulting in a coherent mass by the methods of the invention. The method and apparatus of the invention permit selective, coagulation of a targeted tissue area and not blood or other body fluids which are found external, e.g., surrounding, to the target site.

The term "body fluids" is intended to encompass those naturally occurring physiological components produced by a subject to maintain stasis. These fluids typically include physiological components such as plasma, growth factors, platelets, lymphocytes, granulocytes, etc.

The term "photochemical" is well recognized in the art and includes various energetic processes, including chemical reactions initiated by photons generated by an energy source. Typically photochemical processes are associated with laser, ultra-violet light, visible light or infrared light. Photochemical processes include the generation of radicals by photons colliding with tissue. The radical species are generated within cell tissue, often times causing oxidation of the cell contents; degradation or eradication occurs after the radical species are generated. In the method of the invention, photochemical reactions are selective for the targeted tissue area and not blood or other body fluids which are found external to the targeted treatment site.

Photochemical processes cause injury to cells and tissue either by mechanical lysis or by the generation of by-products such as free radicals, e.g., such as $HO_2.$, $OH^-.$, $HO.$ and $H_2O.$, which damage cell and/or tissue membrane. These reactive by-products can interact with the localized surrounding tissue area such that the tissue is cleansed of unwanted material. Photochemical processes can involve oxidation or radical polymerization of, for example, cell walls, extracellular matrix components, cell nuclei, etc. Such photochemical processes can be induced by infrared, visible and ultraviolet light energy.

The terms "into" and "onto" are used interchangeably and are intended to include treatment of tissue by focusing energy, e.g., ablative, coagulative, or photothermal, toward the afflicted area. In some instances the energy penetrates the tissue and in other instances the energy only superficially treats the surface of the tissue. An ordinary skilled artisan would understand what depths of penetration are required and those parameters which are dependent upon the application, tissue type, area to be treated and severity of condition. Accordingly, the amount of energy used to treat the afflicted area would be attenuated based upon the disease or condition being treated.

"Interstitial cavity," as the term is used herein, encompasses interstices in a tissue or structure of a natural body structure, spaces and gaps existing between layers of tissue or existing within organs, and can include interstices within the interior of the ureter, bladder, intestines, stomach, esophagus, trachea, lung, blood vessel or other organ or body cavity, and will be further understood to include any surgically created interstice that defines an interior cavity surrounded by tissue.

The term "wave guide" is well recognized in the art and is intended to include those devices that constrain or guide the propagation of electromagnetic radiation along a path defined by the physical construction of the guide. Several wave guides are of importance, including hollow-pipe waveguides and dielectric waveguides. Hollow-pipe guides are used primarily in the microwave region of the spectrum, dielectric guides primarily in the optical region. An infinite number of guide shapes are possible, including circular triangular, rectangular, or square and combinations thereof. Consequently, there are an infinite number of projections possible based upon the shape of the wave guide, e.g., annular, e.g., a ring or halo, and the outlines of a triangle, rectangle, or square and combinations thereof.

In preferred embodiments, the electromagnetic radiation, e.g., coherent light, is emitted from the wave guide such that the projected energy expands uniformly over a distance. For example, annular projection of laser light from a circular wave guide forms an expanding cone. The angle of the cone of light is dependent upon the angle of reflection within the wave guide, the concavity of inner walls within the wave guide and the distance to an object to which it is projected. For example, as shown in FIG. 1, optical apparatus 10 includes and optical fiber 12 in communication with an optical wave guide 14 having a concave interior. Modified wave guide 14 projects an annular beam of light through a GRIN lens 26, e.g., a halo, 16 from distal portion 18 of wave guide 14 over a distance, $d_1$. Typically, the angle of projection from the central axis of the optical fiber 12 or wave guide 14 is between about 20 and 45 degrees.

As shown in FIG. 1, the projection of a beam of light from wave guide 14 expands over distance $d_1$, thereby forming an annulus, an outline of a shape formed from light passing through a modified wave guide 14 and GRIN lens 26, having a diameter which is generally larger than the diameter of distal portion 18 of wave guide 14. The diameter of the annular beam of light 16 is dependent upon the distance $d_1$, from the point of projection to point of capture by a surface, e.g., a tissue site, e.g., an interstitial cavity or lumen. The width, $w_2$, of the annulus is dependent upon the width $w_1$ of distal end 18, distance $d_1$, distance $d_2$, and angles $\alpha_1$ and $\alpha_2$. Width $w_2$ is typically between about 0.5 mm to about 5 mm, preferably between about 1 mm to about 4 mm, most preferably between about 2 mm and about 3 mm. Varying angles $\alpha_1$ and $\alpha_2$ and distance $d_2$ maximizes or minimizes angle $\alpha_3$ about the central axis as depicted in FIG. 1. Typically, angle $\alpha_3$ of projected annular light is between about 15 and about 45 degrees, preferably between about 16 and about 30 degrees, most preferably between about 17 and about 25 degrees.

Figure 2:
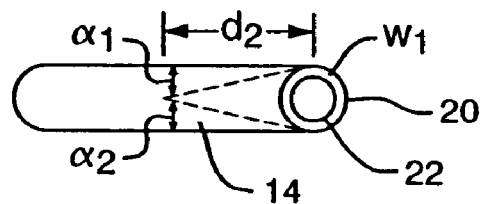
FIG. 2 is a cross sectional view of a modified wave guide of the invention.
Figure 3:
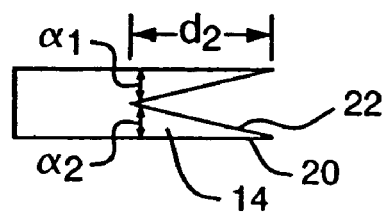
FIG. 3 is another cross sectional view of a modified wave guide of the invention.

As shown in FIGS. 1, 2 and 3, the width, $w_1$, of distal portion 18 can be minimized or maximized depending upon where the modified portion, e.g., the concave portion, within wave guide 14 terminates. Typically widths, $w_1$ as shown in FIGS. 2 and 3, are between about 0.05 mm and about 1.0 mm, inclusive, more preferably between about 0.1 mm and about 0.5 mm, most preferably between about 0.1 mm and about 0.2 mm, inclusive. The distal portion 18, therefore, can be a rim which has substantially no appreciable width, $w_1$, e.g., a point where the exterior wall 20 of wave guide 14 and interior wall 22 intersect (FIG. 3). In general, the diameter of wave guide 14 is between about 0.2 mm to about 1.0 mm, inclusive, more preferably between about 0.3 mm to about 0.8 mm, inclusive, and most preferably between about 0.4 mm to about 0.7 mm, inclusive.

Figure 4:
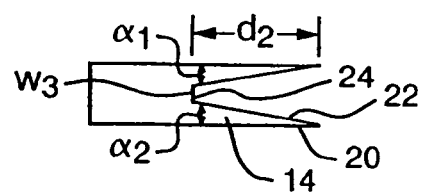
FIG. 4 is still another cross sectional view of a modified wave guide encompassed by the invention.
Figure 5:
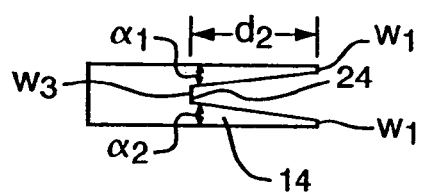
FIG. 5 is yet another cross sectional view of a modified wave guide useful with the present invention.

FIGS. 4 and 5 depict alternative embodiments of modified wave guide 14 where the interior walls 22 of the tapered concave surface meet at position 24 within wave guide 14. In certain embodiments position 24, where the tapered interior walls meet, is centrally located, in other embodiments position 24 can be off axis. In one aspect, position 24, where tapered interior walls 22 meet, is planar and can have a width, $w_3$, which is between about 0.05 mm and about 0.5 mm, inclusive, preferably between about 0.1 mm and about 0.3 mm, inclusive, and most preferably between about 0.2 mm and about 0.3 mm, inclusive. In another aspect, position 24 can be cup shaped. As shown in FIG. 4, distal portion 18 is a rim formed by external wall 20 and interior wall 22. As shown in FIG. 5, distal portion 18 has width, $w_1$, as described above.

Figure 6:
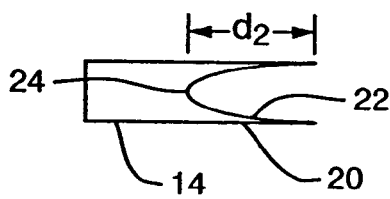
FIG. 6 is still yet another cross sectional view of a modified wave guide useful in the present invention.
Figure 7:
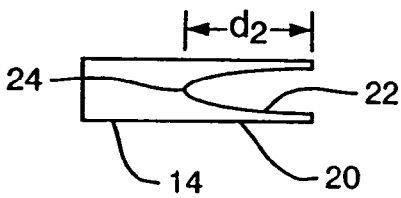
FIG. 7 is another cross sectional view of a modified wave guide of the invention.

FIGS. 6 and 7 depict still other alternative embodiments of wave guide 14 where the interior walls 22 of the tapered concave surface meet at position 24 within wave guide 14. In certain embodiments position 24, where the tapered interior walls meet, is centrally located, in other embodiments position 24 can be off axis. In one aspect, interior walls 22 are asymptotic. As shown in FIG. 6, distal portion 18 is a rim formed by external wall 20 and interior wall 22. As shown in FIG. 7, distal portion 18 has width, $w_1$, as described above.

Wave guides, as described in above and in FIGS. 1-7 can be made from materials known in the art such as quartz, fused silica or polymers such as acrylics. Suitable examples of acrylics include acrylates, polyacrylic acid (PAA) and methacrylates, polymethacrylic acid (PMA). Representative examples of polyacrylic esters include polymethylacrylate (PMA), polyethylacrylate and polypropylacrylate. Representative examples of polymethacrylic esters include polymethylmethacrylate (PMMA), polyethylmethacrylate and polypropylmethacrylate.

Internal shaping of the wave guide can be accomplished by removing a portion of material from a unitary body, e.g., a cylinder or rod. Methods known in the art can be utilized to modify wave guides to have tapered inner walls, e.g., by grinding, milling, ablating, etc. Preferably, a hollow polymeric cylinder, e.g., a tube, is heated so that the proximal end collapses and fuses together, forming an integral proximal portion which tapers to the distal end of the wave guide. In a preferred embodiment, the wave guide is flexible.

Figure 8:
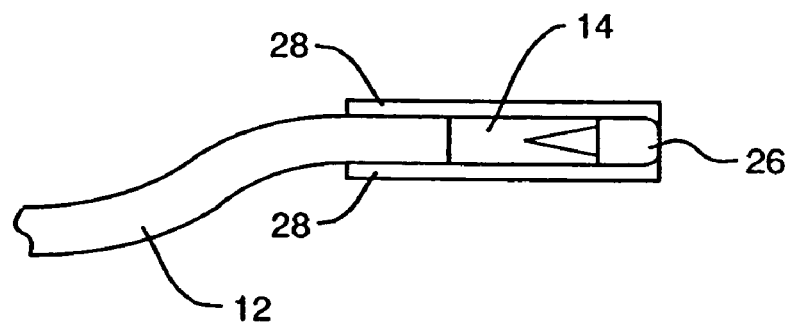
FIG. 8 is an optical apparatus of the invention bonded by a melt formed polymeric material.

Wave guide 14 is in communication, e.g., connected, with optical fiber 12 by methods known in the art. These methods include for example, glueing, or fusing with a torch or carbon dioxide laser. In one embodiment shown in FIG. 8, wave guide 14, optical fiber 12 and, optionally, a gradient index lens (GRIN) 26 are in communication and are held in position by welding with a polymeric material 28, such as TEFLON®, e.g., by melting the polymeric material about the optical apparatus 10 and, optionally, GRIN 26.

The terms "gradient index lens" or "graded index lens" (GRIN) are well recognized in the art and are intended to mean those lenses which have a refractive index distribution, which takes place in a parabolic manner so that the refractive index is greatest at the central axis of the rod and so that the refractive index is progressively reduced from the central axis toward the periphery of the rod. As a result, the penetrating light is caused to move inside the rod in a zigzag manner. The shape of the GRIN lens can be cylindrical, oval, round, or convex.

The term "flexible elongate member" is well recognized in the art and is intended to refer to a hollow tube having at least one lumen. In general, a flexible elongate member is often termed a "catheter", a term which is well known in the art. The flexible elongate member has proximal and distal ends with at least one longitudinal lumen extending therebetween. The distal end can be open or closed as is known in the art. In one embodiment, the distal end of the flexible elongate member is open, thereby allowing an optical apparatus of the invention to protrude beyond the elongate member, e.g., into a catheter end, e.g., into a balloon member. In another embodiment, the distal portion of the elongate member is closed, thereby preventing an optical apparatus from passing beyond the distal end of the elongate member.

Flexible elongate members, e.g., tubular catheters, can be formed from biocompatible materials known in the art such as cellulosic ethers, cellulosic esters, fluorinated polyethylene, phenolics, poly-4-methylpentene, polyacrylonitrile, polyamides, polyamideimides, polyacrylates, polymethacrylates, polybenzoxazole, polycarbonates, polycyanoarylethers, polyesters, polyestercarbonates, polyethers (PEBAX, polyether block amide), polyetherketones, polyetherimide, polyetheretherketones, polyethersulfones, polyethylene, polypropylene, polyfluoroolefins, polyimides, polyolefins, polyoxadizoles, polyphenylene oxides, polyphenylene sulfides, polysulfones, polytetrafluoroethylene, polythioethers, polytraizoles, polyurethanes, polyvinyls, polyvinylidene fluoride, silicones, urea-formaldehyde polymers, or copolymers or physical blends thereof.

Preferably, the materials used to construct the flexible elongate member or the catheter end portion can be "transparent" materials, such as fluoropolymers. Suitable transparent materials include polyethylene, nylon, polyurethanes and silicone containing polymers, e.g., silastic. Suitable fluoropolymers include, for example, fluorinated ethylene propylene (FEP), perfluoroalkoxy resin (PFA), polytetrafluoroethylene (PTFE), and ethylene-tetrafluoroethylene (ETFE). Typically the diameter of the flexible elongate member is between about 0.050 inches and about 0.104 inches, preferably between about 0.060 inches and about 0.078 inches. The diameter of at least one inner lumen of the flexible elongate member is between about 0.030 inches and about 0.060 inches, preferably between about 0.040 inches and about 0.050 inches. The length of the flexible elongate member varies with the intended application and in generally between about 60 cm and about 145 cm in length. For cardiac applications the flexible elongate member is between about 80 cm, and about 125 cm long, for bronchial applications the flexible elongate member is 125 cm long.

The term "catheter" as used herein is intended to encompass any hollow instrument capable of penetrating body tissue or interstitial cavities and providing a conduit for selectively injecting a solution or gas, including without limitation, venous and arterial conduits of various sizes and shapes, bronchioscopes, endoscopes, cystoscopes, culpascopes, colonscopes, trocars, laparoscopes and the like. Catheters of the present invention can be constructed with biocompatible materials known to those skilled in the art such as those listed supra, e.g., silastic, polyethylene, Teflon, polyurethanes, etc.

Typically, the optical apparatus of the invention is positioned proximate to the tissue targeted for treatment within a catheter. The catheter has been positioned proximate to the targeted tissue site and provides that the optical apparatus can be slidably positioned proximate to the tissue, thereby avoiding direct contact with the tissue and/or body fluids. In a preferred embodiment, a balloon is inflated against the tissue, thereby forcing blood and/or body fluids away from the tissue targeted for treatment. Light energy is then passed through the optical apparatus, a GRIN lens and balloon onto the targeted tissue such that an annular image is projected onto the site which causes ablation, coagulation and/or phototherapeutic processes to occur within the tissue.

The term "biocompatible" is well recognized in the art and as used herein, means exhibition of essentially no cytotoxicity while in contact with body fluids or tissues. "Biocompatibility" also includes essentially no interactions with recognition proteins, e.g., naturally occurring antibodies, cell proteins, cells and other components of biological systems.

The term "transparent" is well recognized in the art and is intended to include those materials which allow diffusion of energy through, for example, the flexible elongate member, the tip, cap and/or a catheter end. Preferred energy transparent materials do not significantly impede (e.g., result in losses over 20 percent of energy transmitted) the energy being transferred from a optical apparatus to the targeted tissue or cell site. Suitable transparent materials include fluoropolymers, for example, fluorinated ethylene propylene (FEP), perfluoroalkoxy resin (PFA), polytetrafluoroethylene (PTFE), and ethylene-tetrafluoroethylene (ETFE).

The term "fixedly attached" is intended to include those methods known in the art to attach a catheter end portion, cap, or balloon to the distal portion of a flexible elongate member. Various means are known to those skilled in the art for fixedly attaching individual members of the present apparatus to each other. Such methods include thermal welding or glueing the two materials together to form a uniform seam which will withstand stresses placed upon the integral seam. For example, the catheter end portion or a tip is welded, e.g., thermal, photochemical, sonically, e.g., ultrasound, or glued, at the proximal most portion of the catheter end or tip to the distal end of the flexible elongate member. In another embodiment, the proximal end of the catheter end is affixed to the distal end of the elongate member which is itself a sealed, e.g., having a tip or a cap.

The terms "tip" or "cap" are well recognized in the art and are intended to include those devices which are used to seal the end of a luminal body. In one embodiment, the cap is non-metallic. In certain embodiments, the cap is non-porous. In a preferred embodiment, the cap is non-metallic and non-porous, e.g., a polymeric material.

The term "catheter end portion" is intended to include a separate attachable, and in certain embodiments, detachable, catheter-like portion which is located proximate to the distal end of a catheter. The catheter end portion can be fixedly attached or integrally locked into place on the distal end of a catheter by methods known in the art, e.g., glueing, melting, ultrasonic welding, "snap on" fittings, male-female fittings, etc. Preferably the catheter end portion is energy transparent. An example of a catheter end portion is a silicone balloon anchor.

The term "control handle" is well recognized in the art and is intended to include various means to manipulate the apparatus of the invention, including at least the flexible elongate member, guidewires if present, and the optical apparatus. Various control handles useful with the present invention are commercially available, such as those manufactured by Cordis Webster, Inc., 4750 Littlejohn St., Baldwin Park, Calif., 91706. When used, the control handle applies tension, e.g., stress, to the proximate end of a guidewire, thereby causing the distal end of the guidewire to bend, distort or deform. As a consequence of this action, the flexible elongate member to which the guidewire is attached, also bends, distorts or deforms in the same plane as the guidewire.

The phrase "light transmitting optical fiber" is intended to include those fibers, glass, quartz, or polymeric, which conduct light energy in the form of ultraviolet light, infrared radiation, or coherent light, e.g., laser light.

An exemplary manufacturing process suitable for joining the wave guide to a glassclad or polymer-clad optical fiber having an outer diameter of about 50 to 1,000 micrometers can begin by stripping off a buffer from the end of the fiber, e.g., exposing about 2 or 3 millimeters of the inner fiber core and its cladding. (It is not necessary to strip the cladding away from the core.) Prior to stripping, the fiber end face preferably should be prepared and polished as is known in the art to minimize boundary or interface losses.

In one embodiment, a transparent tubular structure will form a housing and attaching means for the wave guide and prepared fiber end. The fiber and wave guide are positioned such that they located so that the distal end of the stripped fiber and the proximal end of the wave guide are in communication. The tubular structure can be slid over the two components, thereby fixing the respective ends to each other. Preferably, a GRIN lens is placed in communication with the distal end of the wave guide and contained within the tubular structure. In one preferred embodiment, the housing is a Teflon® FEP tubing available, for example, from Zeus Industries (Raritan, N.J.). The transmission spectrum of Teflon® FEP shows that this material is well suited for a scatterer encasing material across a spectrum of light ranging from the infrared to ultraviolet.

Preferred energy sources include laser light, in the range between about 200 nanometers and 10.5 micrometers. In particular, wavelengths that correspond to water absorption peaks are often preferred. Such wavelengths include those between about 900 and about 950 nm, inclusive, preferably 910 and about 920 nm, most preferably, 915 nm. Suitable lasers include excimer lasers, gas lasers, solid state lasers and laser diodes. A particularly preferred AlGaAs diode array, manufactured by Optopower, Tucson, Ariz., produces a wavelength of 915 nm. A preferred energy is coherent light, e.g., laser light, in the range between about 200 nm to about 2.4 µm, preferably between about 400 to about 3,000 nm, more preferably between about 805 and 1060 nm. Typically the conductor emits between about 2 to about 10 watts/cm of length, preferably between about 4 to about 6 watts/cm, most preferably about 4 watts/cm.

In one embodiment, the optical apparatus can extend beyond the distal end of the flexible elongate member. In certain embodiments, the optical apparatus slidably extends into a lumen created by a balloon filled with a suitable solution or gas. Alternatively, the optical apparatus can be slidably located or fixed within a transparent flexible elongate member about which surrounds an inflated balloon. In this embodiment, the light is projected annularly through the transparent flexible elongate member, through an inflation solution and into the inflated balloon and onto the targeted treatment site.

The light transmitting optical fiber transmits the energy from an energy source which is in communication with the optical fiber. Suitable energy sources are known in the art and produce the above-mentioned types of energy. Preferred laser sources include diode lasers. The optical fiber is positioned within lumen formed by a flexible elongate member (described supra). The optical fiber can be slidably controlled within the lumen such that positioning of the optical fiber within the flexible elongate member is readily achieved. Preferably, the optical fiber is positioned proximate to the expanded balloon member.

The balloon, e.g., a biocompatible balloon, is affixed to the catheter body member near the distal end and is in fluid communication with at least one of inflation port. Upon injection of solution, the expandable balloon inflates forming a lumen or "reservoir" between the catheter body and the outerwall of the balloon. It should be understood that the term "balloon" encompasses deformable hollow shapes which can be inflated into various configurations including balloon, circular, tear drop, etc., shapes dependent upon the requirements of the body cavity.

The terms "treat", "treatment" or "treating" are intended to include both prophylactic and/or therapeutic applications. The methods of the invention can be used to protect a subject from damage or injury caused by a disease, physical aberration, electrical aberration, or can be used therapeutically or prophylactically treat the subject after the onset of the disease or condition.

The term "subject" is intended to include mammals susceptible to diseases, including one or more disease related symptoms. Examples of such subjects include humans, dogs, cats, pigs, cows, horses, rats and mice.

The term "tissue" is well recognized in the art and is intended to include extracorporeal materials, such as organs, e.g., mesentery, liver, kidney, heart, lung, brain, tendon, muscle etc.

The term "disease" is associated with an increase of a pathogen within a subject such that the subject often experiences physiological symptoms which include, but are not limited to, release of toxins, gastritis, inflammation, coma, water retention, weight gain or loss, ischemia and immunodeficiency. The effects often associated with such symptoms include, but are not limited to fever, nausea, diarrhea, weakness, headache and even death. Examples of diseases which can be treated by the present invention include undesirable cell proliferation, bacterial infection, cancer, e.g., bladder, urethral, mammarian, ovarian and lung cancer, or, ischemia, and benign prostatic hypertrophy or hyperplasia (BPH).

The language "undesirable cell proliferation" is intended to include abnormal growth of cells which can be detrimental to a subject's physiological well being. Effects of undesirable cell proliferation can include the release of toxins into the subject, fever, gastritis, inflammation, nausea, weakness, coma, headache, water retention, weight gain or loss, immunodeficiency, death, etc. The undesired cells which proliferate can include cells which are either benign or malignant. Examples of undesirable cell proliferation include bacterial cell proliferation and aberrant cell division and/or proliferation of foreign cells, such as in cancer cells.

The terms "aberrant cell" or "aberrant tissues" as used herein, are well recognized in the art and are intended to include aberrant cell division and/or proliferation where cells are generated in excess of what is considered typical in physiologically similar environment, such as in cancers.

The language "control of undesirable cell proliferation" or "controlling undesirable cell proliferation" is intended to include changes in growth or replication of undesired cells or eradication of undesired cells, such as bacteria, cancer, or those cells associated with abnormal physiological activity. The language includes preventing survival or inhibiting continued growth and replication of an undesired cell. In one preferred embodiment, the control of the undesired cell is such that an undesired cell is eradicated. In another preferred embodiment, the control is selective such that a particular targeted undesired cell is controlled while other cells, which are not detrimental to the mammal, are allowed to remain substantially uncontrolled or substantially unaffected, e.g., lymphocytes, red blood cells, white blood cells, platelets, growth factors, etc.

The term "cancer" is well recognized in the art and is intended to include undesirable cell proliferation and/or aberrant cell growth, e.g., proliferation.

The term "modulate" includes effect(s) targeted tissue(s) that prevent or inhibit growth of diseased tissue, which may ultimately affect the physiological well being of the subject, e.g., in the context of the therapeutic or prophylactic methods of the invention.

The term "solution" is intended to include those solutions, e.g., aqueous solutions, which can be administered to a subject through a device of the present invention without subsequent adverse effects. In particular, the solution should not diminish the strength, quality, or wavelength of energy emitted, e.g., laser energy, from the optical apparatus. In general, the solution is considered a pharmaceutically acceptable carrier or vehicle.

Each solution must be "acceptable" in the sense of not being injurious to the patient. Some examples of materials which can serve as acceptable carriers include excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

The solution can also include adjuvants such as wetting agents, emulsifying and suspending agents, lubricants, such as sodium lauryl sulfate and magnesium stearate, as well as coloring agents, release agents, coating agents, preservative agents and antioxidants can also be present in the solutions.

Examples of pharmaceutically acceptable antioxidants useful in the solutions include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Solutions useful in the methods of the invention include emulsions, microemulsions, solutions, suspensions, syrups and elixirs. The solution may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

The term "modify" is intended to encompass those changes the targeted tissue site, e.g., the surface, that cause the tissue to no longer have undesired properties. For example, treatment of the anterior wall of the right atrium by the present invention changes the path of electrical conduction after photonic treatment. The result is a conduction block which redirects conduction through the tissue and prevents the conduction from traveling across the atrial wall as it did prior to treatment.

The present invention also pertains to methods for forming an annular lesion in a tissue by ablation, coagulation and/or phototherapeutic processes. The methods introduce an optical apparatus proximate to a tissue site via, for example, a catheter. The optical apparatus includes a modified optical wave guide that is in communication with a light transmitting optical fiber. Energy is transmitted through the optical fiber, such that radiation propagating through the optical fiber and wave guide projects an annular light pattern, e.g., a circle, ring, halo or an outline or a shape formed by and projected from the modified wave guide. Preferably, the light is projected through a graded intensity lens that is adjacent to the optical wave guide. This additional step attenuates aberrations in the light pattern and facilitates the forward annular projection of the therapeutic light. By these methods, an annular lesion can be formed in tissue. In certain embodiments, the tissue forms a lumen, e.g., vascular, atrial, brachial, uretral, etc.

The present invention further pertains to methods for forming annular lesions in cardiac tissue, e.g., trabecular tissue, by ablation, coagulation and/or phototherapeutic processes. The methods include introduction of an optical apparatus proximate to cardiac tissue via, for example, a catheter. The optical apparatus includes an optical wave guide in communication with a light transmitting optical fiber and preferably, a GRIN lens. Energy is transmitted through the optical fiber, such that radiation propagated through the optical fiber, wave guide and GRIN lens is forwardly projects an annular light pattern, e.g., a circle or a halo. By these methods, an annular lesion can be formed in cardiac tissue.

The term "trabecular" is well recognized in the art and is intended to include tissue, e.g., cardiac tissue, which is a elastic tissue often formed of bands and cords called trabeculae consisting of fibrous tissue, elastic fibers and muscle fibers.

The present invention also pertains to methods for treating or preventing atrial arrhythmias by ablation, coagulation or photochemical processes. The methods include introducing an optical apparatus proximate to atrial tissue via, for example, a catheter. The optical apparatus includes an optical wave guide in communication with a light transmitting optical fiber. Energy is transmitted through the optical fiber, such that radiation propagating through the optical fiber and wave guide projects an annular light pattern. The annular light pattern forms an annular lesion in the atrial tissue, thereby treating or preventing atrial fibrillation. The methods of the invention can be performed therapeutically or prophylactically.

Atrial fibrillation and atrial flutter are abnormalities in the rhythm or rate of the heart beat. For an adult at rest, the heart normally beats between 60 and 80 beats per minute, but when atrial fibrillation occurs, the atria may beat irregularly and very rapidly between 350 and 600 times per minute. This causes the ventricles to beat irregularly in response as they try to keep up with the atria. Atrial flutter is similar to atrial fibrillation. The atrial contractions are less rapid, however, usually between 200 to 400 beats per minute, and are regular. Atrial flutter is often associated with a heart attack or may occur after heart or lung surgery. Atrial fibrillation often results from a myriad of heart conditions such as angina, tachycardia, heart attack, heart valve problems, and even high blood pressure. All of these conditions can cause stretching and scarring of the atria that interfere with the heart conduction system. The heart muscle can be weakened if episodes lasting several months or longer (with rapid heart rates) occur. Briefer episodes only cause problems if the heart rate is very fast or if the patient has a serious heart problem in addition to the atrial fibrillation.

Figure 9:
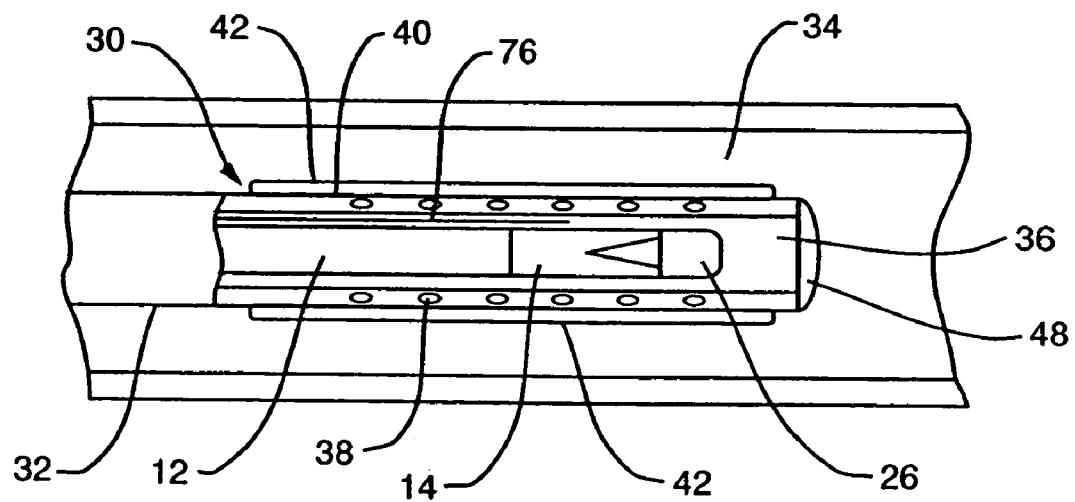
FIG. 9 is a cross-sectional view of the distal end portion of an embodiment of the invention having an optical apparatus and a balloon contained within a tubular body lumen in an uninflated state.
Figure 10:
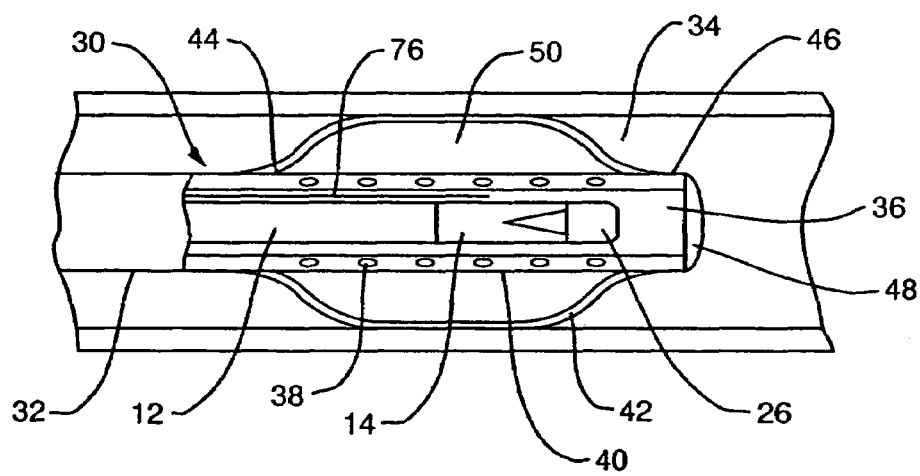
FIG. 10 is a cross-sectional view of the device of FIG. 9 following inflation of the balloon.

In FIGS. 9 and 10, apparatus 30, constructed in accordance with the present invention, is depicted in its unexpanded and expanded form within a body cavity such as a lumen of a blood vessel 34. Flexible elongate member 32 includes at least one lumen 36 extending the length thereof from a proximal end to a distal end and can include, optionally, cap 48. Openings 38 in the side wall of the flexible elongate member 32 define one or more pores that provide fluid communication between the lumen 40 and an outer balloon 42, which can be bonded at proximal end 44 and distal end 46 to flexible elongate member 32. Optical apparatus 10 can be slidably positioned within lumen 36 adjacent to balloon 42. Apparatus 30 can further include reflectance fiber 76 to monitor the progress of treatment as described infra. Optical apparatus 10 includes optical fiber 12, modified wave guide 14 and GRIN lens 26. As shown in FIG. 10, injection of fluid or gas, through lumen 40 and pores 38, forces the fluid or gas to flow out of the pores 38 to fill the chamber 50 within the balloon 42, thereby inflating balloon 42. In a preferred embodiment, the balloon is spherical or tear drop shaped. Preferably, flexible elongate member 32 and balloon 42 are energy transparent.

By injecting a suitable solution or gas into chamber 50, balloon 42 can be inflated to engage body tissue (e.g., the interior surface of a blood vessel or other body lumen or tissue surrounding a natural or excised interstitial space within the body). In one embodiment, balloon 42 is non-porous and can engage the body tissue over a substantial portion of its length, thereby eliminating blood and/or other body fluids.

Figure 11:
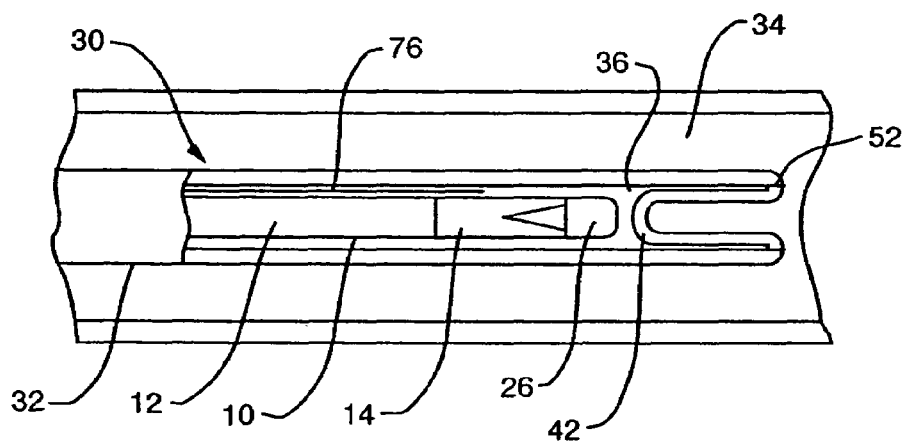
FIG. 11 is a cross-sectional view of another intraluminal device of the invention with the balloon in an uninflated stated and stowed within the lumen of the flexible elongate member.
Figure 12:
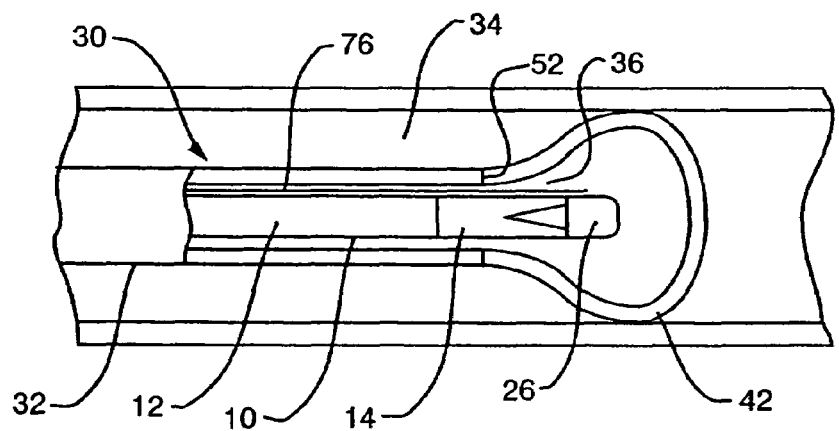
FIG. 12 is a cross-sectional view of a catheter device of FIG. 11 after a gas or solution has been added through the lumen of the flexible elongate member.

In FIG. 11, apparatus 30, constructed in accordance with the present invention, is depicted in its deflated position. Balloon 42 resides within lumen 36 of flexible elongate member 32 and is fixedly attached at distal end 52. Apparatus 30 can further include reflectance fiber 76 to monitor the progress of treatment as described infra. As a solution or gas is injected through lumen 36, balloon 42 expands outwardly from flexible elongate member 32 as shown in FIG. 12. Optical apparatus 10 can be slidably positioned within lumen 36 within balloon 42. Optical apparatus 10 includes optical fiber 12, modified wave guide 14 and GRIN lens 26. The expansion of balloon 42 is dependent upon the length of balloon 42, the type of balloon material and the applied pressure of solution or gas. By this method, balloon 42 can conform to the body cavity to which it is proximate. In a preferred embodiment, balloon 42 is non-porous. Preferably, flexible elongate member 32 and balloon 42 are energy transparent.

Figure 13:
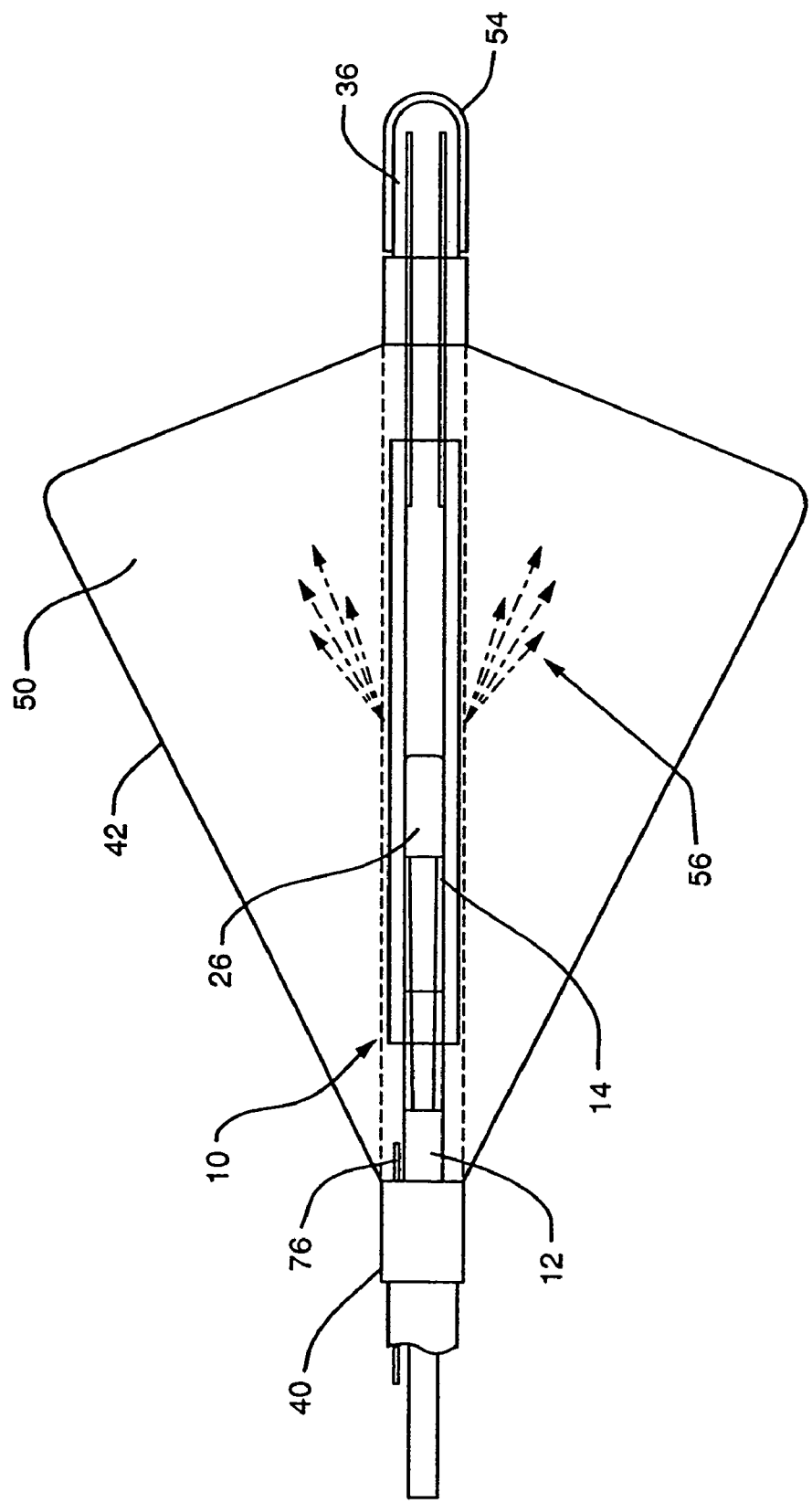
FIG. 13 is a cross-sectional view of a preferred device of the invention including an inflated balloon attached to a flexible elongate member having an optical apparatus contained therein.
Figure 13A:
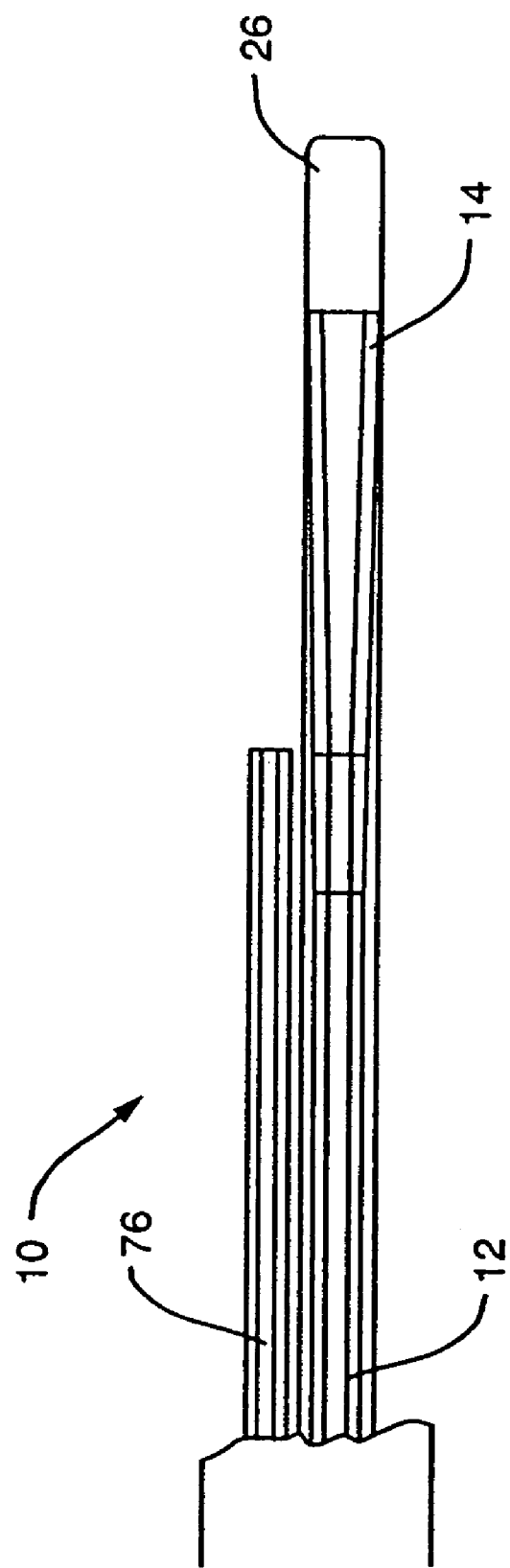
FIG. 13A is an expanded cross-sectional view of the optical apparatus of FIG. 13.

A preferred embodiment is depicted in FIGS. 13 and 13A having a silicone balloon anchor 54 (not inflated). Optical apparatus 10 can be slidably positioned within lumen 36 adjacent to balloon 42. Optical apparatus 10 includes optical fiber 12, modified wave guide 14 and GRIN lens 26. Gas, e.g., air, or a liquid can be injected into lumen 36 (shown partially in phantom) to inflate silicone balloon anchor 54 if required. A solution, e.g., water, saline, is injected through lumen 40 to inflate balloon 42. Apparatus 30 can further include reflectance fiber 76 to monitor the progress of treatment as described infra. In one embodiment, balloon 42 is preshaped to form a parabolic like shape. This is accomplished by shaping and melting a TEFLON® film in a preshaped mold to effect the desired form. The difference in refractive index between the gas or liquid within lumen 36 and the liquid in chamber 50 facilitates the projection of annular light beam 56 to be emitted at a radical angle from either wave guide 14 through GRIN lens 26.

The devices described in FIGS. 1-13 can be used for treating, e.g., ablating, coagulating and/or phototherapeutically treating endocardial surfaces which promote arrhythmias or other disease states or conditions. For example, atrial therapies can be performed by inserting an apparatus of the invention 30 into the femoral vein. Flexible elongate member 32 having balloon 42 fixedly attached is guided through the inferior vena cava, and into the right atrium, and if required, it is guided into the left atrium via atrial septal puncture. Left ventricular treatment can be performed by inserting flexible elongate member 32 into the femoral artery. Flexible elongate member 32 is guided through the iliac artery, the aorta, through the aortic valve and into the left ventricle. Once balloon 42 is proximate to the tissue ablation site, a solution can be injected through lumen 36 or 40 to force blood and/or body fluids away from the treatment site. Optical apparatus 10 is guided through flexible member 32 via lumen 36 to a position proximate to the tissue ablation site and energy, e.g., laser energy, is emitted through balloon 42. Preferably, the composition of flexible elongate member 32 and balloon 42 are transparent to the energy emitted through optical apparatus 10.

Figure 14:
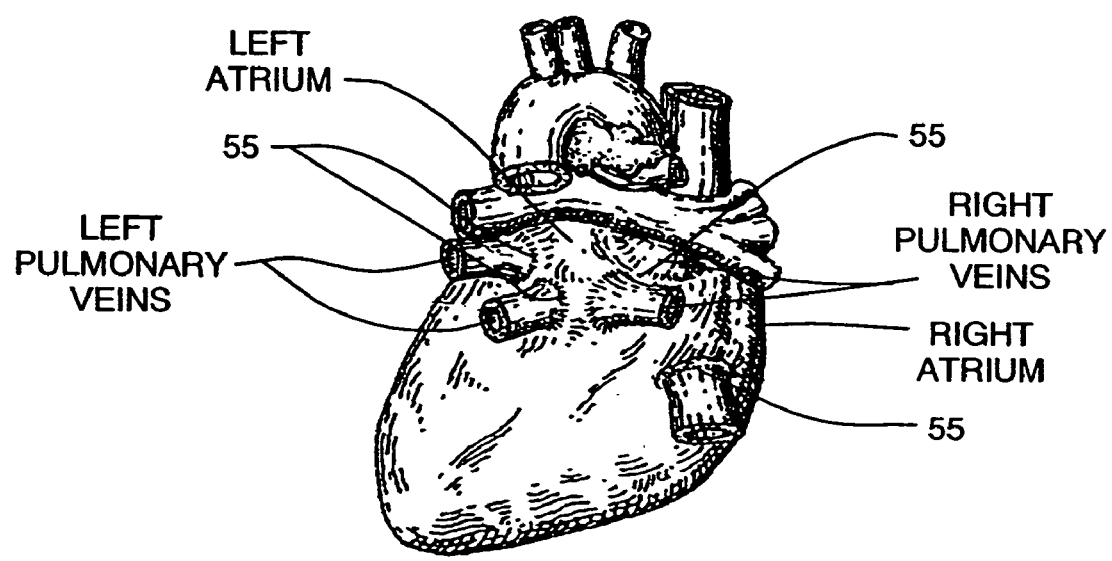
FIG. 14 is a depiction of annular lesions located at the atrium/pulmonary vein interface.

FIG. 14 depicts annular lesions 55 formed on the inside of pulmonary veins by the above described methods. It is considered advantageous to form the annular lesions 55 on the atrial surface/vein interface, thereby preventing propagation of aberrant electrical waves through the cardiac region. Preferably, the lesion(s) completely encircles the inner lumen of the vein(s).

In the present invention, reflective feedback is used to monitor the state of coagulation, ablation and/or phototherapeutic processes of the treatment site so as to allow an optimal dose by either manipulation of the energy level or exposure time, or by controlling the sweep of energy across an exposure path.

Reflectance changes can also be employed by a control means in the present invention to adjust or terminate laser operation.

In another aspect of the invention, a real-time display means can be incorporated into a surgical microscope or goggles worn by a clinician during the procedure to provide a visual display of the state of tissue coagulation simultaneously with the viewing of the surgical site. The display can reveal reflectance values at one or more specific wavelengths (preferably, chosen for their sensitivity to the onset and optimal state of tissue modification), as well as display a warning of the onset of tissue carbonization.

In one method, according to the invention, application of laser to a biological structure(s) while the reflectance of light from the irradiated site is monitored. Changes in scattering due to coagulation, ablation, phototherapeutic effects or crosslinking of the tissue will cause a reflectance change. In addition, dehydration due to laser exposure also affects the site's reflection. The reflectance can be monitored in real-time to determine the optimal exposure duration or aid as visual feedback in the timing used in sweeping the energy across the treatment site during the procedure.

Figure 15:
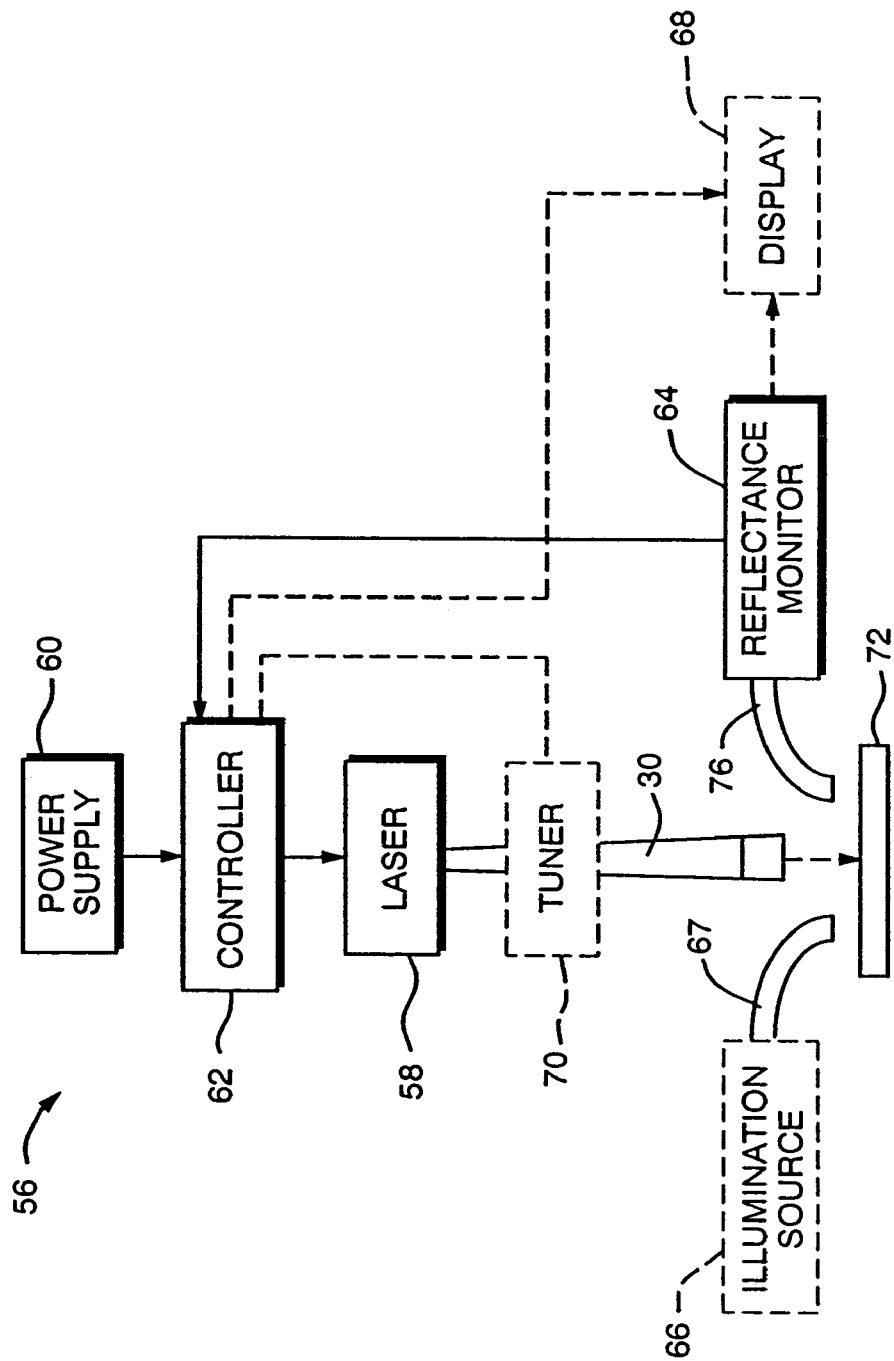
FIG. 15 is a schematic block diagram of a laser tissue treatment system according to the present invention.

In FIG. 15, a schematic block diagram of a laser tissue treatment system 56 is shown, including a laser 58, power supply 60, controller 62 and reflectance monitor 64. The system further includes optical apparatus 30, and, optionally, illumination source 66, display 68 and/or tuner 70. In use, the output of laser 58 is delivered, preferably via optical apparatus 30, to treatment site 72 to phototherapeutically treat selected tissue. As the laser beam irradiates treatment site 72 the biological tissue of the site is coagulated, ablated and/or phototherapeutically treated. The degree of treatment is determined by the reflectance monitor 64, which provides electrical signals to controller 62 in order to control the procedure. The reflectance monitor 64 receives light reflected by the site from a broadband or white light illumination source 66 via fiber 67 and/or from laser 58 via optical apparatus 30. In addition to controlling the laser operation automatically, the reflectance monitor 64 and/or controller 62 can also provide signals to a display 68 to provide visual and/or audio feedback to the clinical user. Optional tuner 70 can also be employed by the user (or automatically controlled by controller 62) to adjust the wavelength of the annealing radiation beam.

Figure 16:
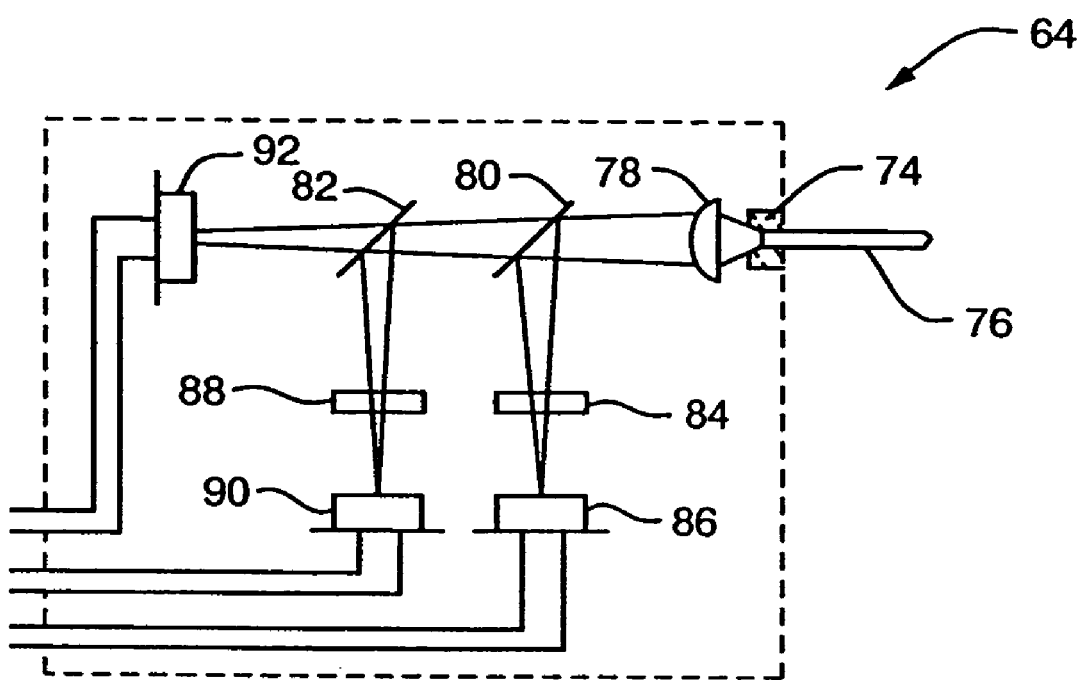
FIG. 16 is a detailed schematic diagram of a reflectance monitor for use in the present invention.

FIG. 16 is a more detailed schematic diagram of a reflectance monitor 64, including a coupling port 74 for coupling with one or more fibers 76 to receive reflectance signals. A preferred reflectance fiber is a 100 micron diameter silica pyrocoat fiber from Spectran (Spectran, Conn., part number CF04406-11). The reflectance monitor 64 can further include a focusing lens 78 and first and second beam splitting elements 80 and 82, which serve to divide the reflected light into 3 (or more) different beams for processing. As shown in FIG. 16, a first beam is transmitted to a first optical filter 84 to detector 86 (providing, for example, measurement of reflected light at wavelengths shorter than 0.7 micrometers). A second portion of the reflected light signal is transmitted by beam splitter 82 through a second optical filter 88 to detector 90 (e.g., providing measurement of light at wavelengths shorter than 1.1 micrometers). Finally, a third portion of the reflected light is transmitted to photodetector 92 (e.g., for measurement of reflected light at wavelengths greater than 1.6 micrometers). Each of the detector elements 86, 90 and 92 generate electrical signals in response to the intensity of light at particular wavelengths.

The detector elements 86, 90 and 92 preferably include synchronous demodulation circuitry and are used in conjunction with a modulated illumination source to suppress any artifacts caused by stray light or the ambient environment. (It should be apparent that other optical arrangements can be employed to obtain multiple wavelength analysis, including the use, for example, of dichroic elements, either as beam splitters or in conjunction with such beam splitters, to effectively pass particular wavelengths to specific detector elements. It should also be apparent that more than three discreet wavelengths can be measured, depending upon the particular application.) The signals from the detector elements can then be transmitted to a controller and/or a display element (as shown in FIG. 15).

In the controller, signals from the reflectance monitor are analyzed to determine the degree of coagulation, ablation and/or phototherapeutic effect(s) which is occurring in the biological tissue exposed to the laser radiation. Typically, such treatment is performed for 100 seconds or less. Such analysis can generate control signals which will progressively reduce the laser output energy over time as a particular site experiences cumulative exposure. The control signals can further provide for an automatic shut-off of the laser when the optimal state of treatment has been exceeded and/or the onset of carbonization is occurring.

In use, the apparatus of the present invention can be employed to analyze the degree of treatment by comparing the reflectance ratios of a site at two or more wavelengths. Preferably, intensity readings for three or more wavelength ranges are employed in order to accurately assess the degree of treatment and to ensure that the optimal state is not exceeded. The particular wavelengths to be monitored will, of course, vary with the particular tissue undergoing treatment. Although the tissue type (e.g., bloodcontaining tissue or that which is relatively blood-free) will vary, the general principles of the invention, as disclosed herein, can be readily applied by those skilled in the art to diverse procedures in which the phototherapeutic treatment of biological materials is desired.

Those skilled in the art will know, or be able to ascertain, using no more than routine experimentation, many equivalents to the specific embodiments of the invention described herein. These and all other equivalents are intended to be encompassed by the following claims. All publications and references cited herein including those in the background section are expressly incorporated herein by reference in their entirety.

What is claimed is:

1. A cardiac ablation instrument, comprising:
a catheter body adapted for insertion into a heart;
an energy emitter slidably adjustable within the catheter body for transmitting energy to a target tissue;
an inflatable balloon coupled to the catheter body and adapted to engage cardiac tissue near the target tissue; and
a lens element disposed within the catheter body and adjacent to the energy emitter, the lens element adapted for projecting a pattern of treatment radiation around at least a portion of the target tissue.

2. The instrument of claim 1, wherein the instrument further comprises a positioning element to modify the path of projected energy.

3. The instrument of claim 1, wherein the instrument is configured to create a lesion on an atrial wall.

4. The instrument of claim 1, wherein the instrument is configured to create a lesion around a pulmonary vein.

5. The instrument of claim 1, wherein the instrument is configured to create a lesion at an interface between a pulmonary vein and an atrial wall region.

6. The instrument of claim 1, further comprising a sensor for detecting energy reflected from target tissue.

7. The instrument of claim 1, further comprising a sensor adapted to monitor ablation based on reflected energy.

8. The instrument of claim 1, wherein lens element is adapted to project an annular lesion on the target tissue.

9. The instrument of claim 1, wherein the lens element is adapted to project a lesion of variable size on the target tissue.

10. The instrument of claim 1, wherein the instrument is adapted to project energy forward.

11. The instrument of claim 1, wherein the instrument is adapted to project energy forward at an angle from a central axis of the catheter body.

12. The instrument of claim 1, wherein the target tissue is a pulmonary vein.

13. A cardiac ablation instrument, comprising:
a catheter body adapted for insertion into a heart;
an energy emitter slidably adjustable within the catheter body for transmitting energy to a target tissue;
an inflatable balloon coupled to the catheter body and adapted to engage cardiac tissue near the target tissue, and further adapted to clear a transmission pathway for projecting the ablative energy from the energy emitter to the target tissue, and
a lens element disposed within the catheter body and adjacent to the energy emitter, the lens element adapted for projecting a pattern of treatment radiation around at least a portion of the target tissue.

14. The instrument of claim 13, wherein lens element is adapted to project an annular lesion on the target tissue.

15. The instrument of claim 13, wherein the lens element is adapted to project a lesion of variable size on the target tissue.

16. The instrument of claim 13, wherein the instrument is adapted to project energy forward.

17. The instrument of claim 13, wherein the instrument is adapted to project energy forward at an angle from a central axis of the catheter body.

18. The instrument of claim 13, wherein the target tissue is a pulmonary vein.

19. A phototherapeutic apparatus comprising
a laser for delivering laser energy to a target tissue;
a flexible elongate catheter, adapted for insertion in a heart via a blood vessel, having a lumen housing a light transmitting optical fiber and an optical lens element for projecting an annular pattern of light onto said target tissue, said optical fiber and optical lens element in communication with said laser such that radiation propagating through said optical fiber is transmitted into the lens element and then projected by the lens element in an annular pattern of phototherapeutic radiation around the target tissue, wherein the optical fiber is slidably adjustable within the lumen and the target tissue is a pulmonary vein;
a reflectance sensor for measuring intensity of light reflected from said tissue while illuminating said tissue;
a momtor connected to said reflectance sensor for monitoring changes in the intensity of light reflected from said tissue;
an analyzer connected to said monitor for determining the degree of therapeutic treatment based upon said monitored changes in said tissue; and
a controller connected to said analyzer and laser for controlling the output of said laser in response to said reflected light from said treated tissue.

* * * * *

UNITED STATES PATENT AND TRADEMARK OFFICE
CERTIFICATE OF CORRECTION

PATENT NO.        : 7,357,796 B2                                      Page 1 of 1
APPLICATION NO. : 11/059423
DATED             : April 15, 2008
INVENTOR(S)       : Norman E. Farr and William E. Wieler It is certified that error appears in the above-identified patent and that said Letters Patent is hereby corrected as shown below:

On the Title page:

In item (73), change "CardioFocus Corporation". to --CardioFocus, Inc.--

In the Claims:

In column 20, Claim 19, line 36, following "a" and prior to "connected", change the word "momtor" to --monitor--.

Signed and Sealed this

Sixteenth Day of September, 2008

JON W. DUDAS
*Director of the United States Patent and Trademark Office*